US00PP09907P

United States Patent [19]

Hein

[11] Patent Number: Plant 9,907

[45] Date of Patent: Jun. 3, 1997

[54] APPLE TREE: 'HEIN' CULTIVAR

[75] Inventor: Robert J. Hein, Tieton, Wash.

[73] Assignee: Columbia Basin Nursery, Quincy, Wash.

[21] Appl. No.: 590,709

[22] Filed: Jan. 17, 1996

[51] Int. Cl.[6] ..... A01H 5/00

[52] U.S. Cl. ..... Plt./34.1

[58] Field of Search ..... Plt./34.1, 35, 35.1

*Primary Examiner*—James R. Feyrer

*Attorney, Agent, or Firm*—Christensen O'Connor Johnson & Kindness

[57] ABSTRACT

The Hein Cultivar is a new variety of apple tree, similar to Golden Delicious and other predominantly yellow-fruited cultivars, characterized by an attractive pink blush on exposed fruits, freedom from russet, and with maturity two weeks later than Golden Delicious.

8 Drawing Sheets

The Hein cultivar is a new variety of apple *Malus pumila* tree, similar to Golden Delicious and other predominantly yellow-fruited cultivars, characterized by an attractive pink blush on exposed fruits, freedom from russet, and with maturity two weeks later than Golden Delicious.

DISCOVERY AND ASEXUAL REPRODUCTION OF THE TREE

I discovered the new variety, a chance seedling, growing from a pile of discarded fruit adjacent to storage sheds on my farm at 1010 Upland Way, Tieton, ten miles east of Yakima, Yakima County, State of Washington, in 1985. The seedling had gone unnoticed for perhaps ten years before this time, until friends and workers noticed the fruit and preferred it to the other commercial varieties growing at the farm. The original tree remains in its original location.

This new variety has been asexually reproduced by bark graft and budding through four generations, and fruited through three successive generations. The characteristics of this variety have remained the same in the progeny trees. The varietal name "Hein Cultivar" is proposed for the subject apple tree.

SUMMARY OF THE TREE

Since the variety is similar to Golden Delicious and other predominantly yellow-fruited cultivars, I have documented the distinct differences between Hein Cultivar and other yellow-fruited cultivars maturing at a similar season (September–October). The results are shown in FIG. 1.

Thus, as shown in FIG. 1, Hein Cultivar matures about 14 days later than Golden Delicious, similar to Blushing Golden and Firmgold. Blushing Golden has a distinctly more yellow ground color and a redder blush (Hein Cultivar has a pink blush), and is somewhat more elongated. Firmgold has a much longer stem and rarely is blushed.

Though not compared directly, Hein Cultivar also is distinctly different in either appearance or maturity from all strains of Golden Delicious and from other yellow-skinned varieties, e.g., Ozark Gold, Magnolia Gold, Hawaii, Earligold, Ginger Gold, New Gold, Suncrisp, and MollyGold.

BRIEF DESCRIPTION OF THE FIGURES

The accompanying table and photographs illustrate distinguishing characteristics of this new variety.

FIG. 7 is transverse and longitudinal sections of a Hein Cultivar apple showing core, seeds, and core lines, Oct. 14, 1994.

DETAILED BOTANICAL DESCRIPTION OF THE HEIN CULTIVAR TREE

Parentage: Chance seedling.

Location of parent tree: Edge of shop buildings at 1010 Upland Way, Tieton, Wash. 98974, U.S.A.

Date of discovery: 1985.

Date of fruit maturity: Approximately 10 to 14 days after Golden Delicious, using pressure, soluble solids, and starch disappearance as primary indicators of maturity. May require two picks to obtain minimum quantity of blushed fruit.

Tree: Large; medium vigorous; spreading, round-topped tall; hardy, productive.

Trunk: Stocky, medium smooth.

Branches: Medium thickness; smooth; much branching; two-year-old wood color is #28-14 Munsell Color Cascade; lenticels medium in number and size, cream-colored, elongated.

Leaves:

*Length.*—95 mm.

*Width.*—45 mm; acute to narrow acute; taper pointed.

*Petiole.*—35 mm, medium thickness (more than Golden Delicious).

*Margin.*—Crenate to finely serrate.

*Color.*—Medium to dark green, upward folding.

Flowers: Mid-season blooming, full bloom April 18–22 at Tieton, Wash.

*Size.*—Medium

*Color.*—White, with pink on reverse side.

*Stamen.*—Single row, anthers yellow turning brown with pollen shed.

*Pistil.*—Stigmas broad, flat at top, rounded at base; styles medium long, fused at base.

*Sepals.*—Medium size; pubescent.

*Pollination requirements.*—Satisfied by other diploid cultivars; self-unfruitful.

Fruit:

*Maturity when described.*—Prime harvest maturity for long-term storage — Oct. 14, 1995; starch content 2.5–3.0.

*Size.*—Axil diameter 63–76 mm (2.5–3.0"); transverse 76–89 mm (3.0–3.5"), similar to Golden Delicious and other Golden-type cultivars.

Figure 2:
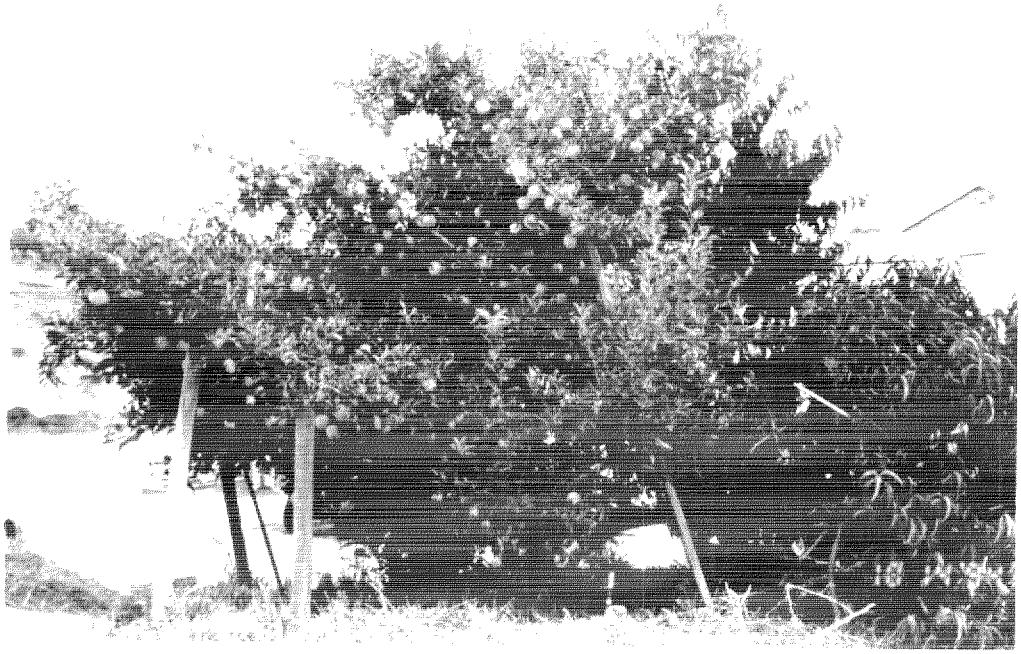
FIG. 2 is the original tree of Hein cultivar at Tieton, Wash., October 1994.
Figure 3:
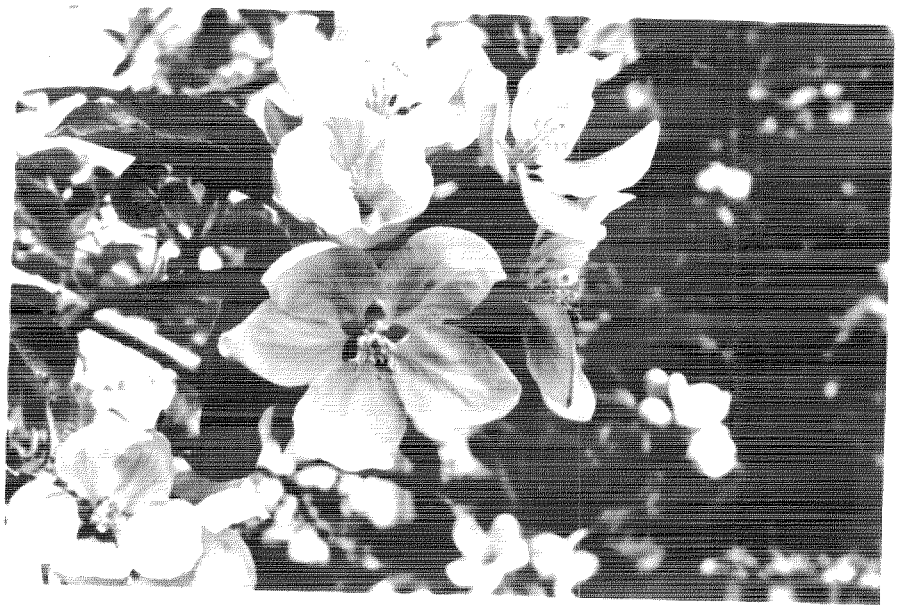
FIG. 3 is a close-up of a Hein cultivar flower cluster, April 1995.
Figure 4:
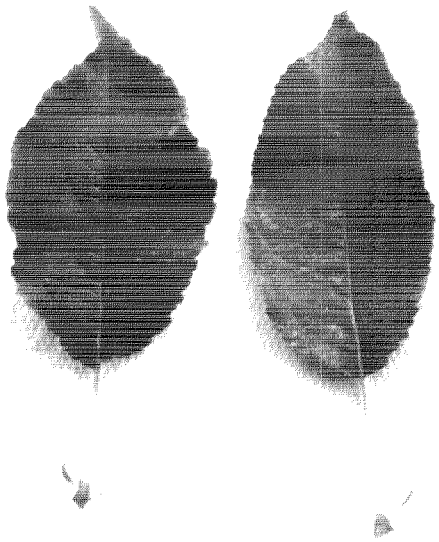
FIG. 4 is the upper leaf surface, mature leaves, July 1995.
Figure 5:
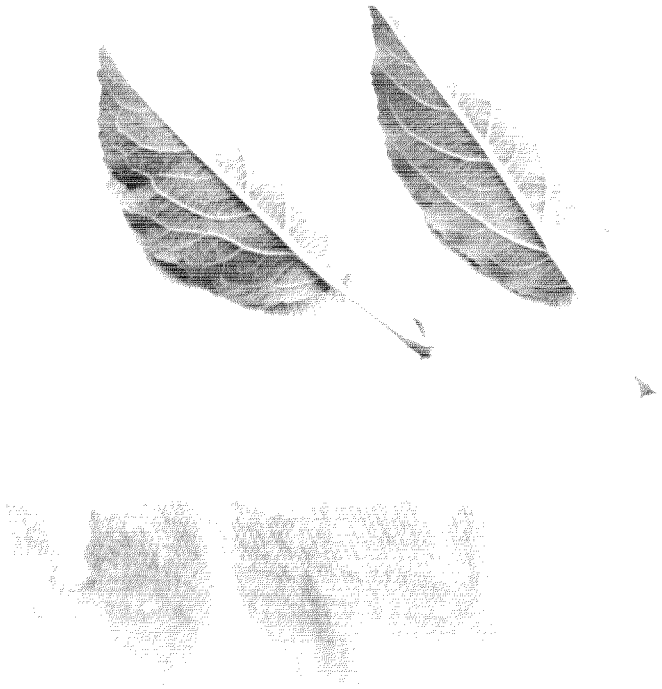
FIG. 5 is the lower leaf surface, mature leaves, July 1995.
Figure 6:
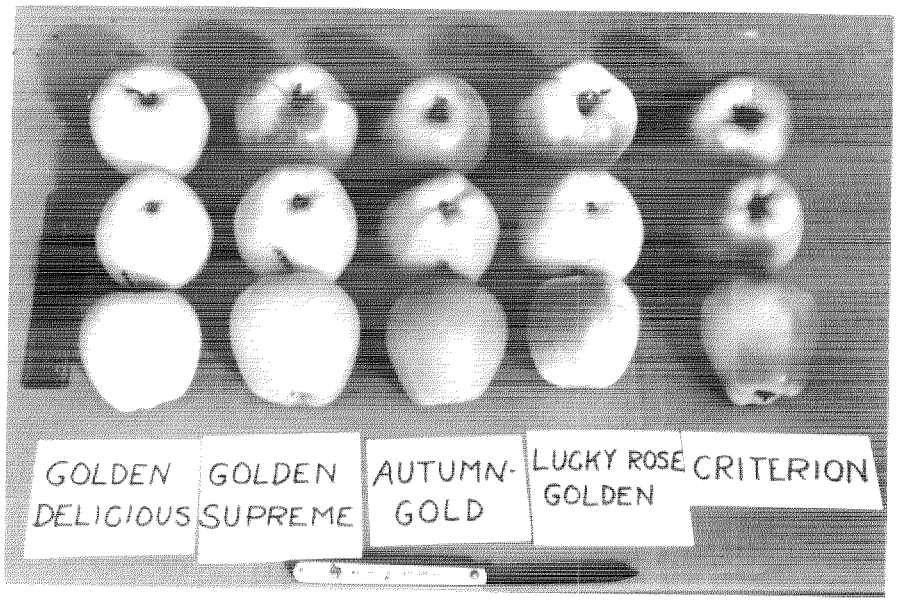
FIG. 6 is a comparison of Hein cultivar apples ("Autumn Gold") with other similar Golden Delicious-type apples, Oct. 13, 1995.
Figure 1:
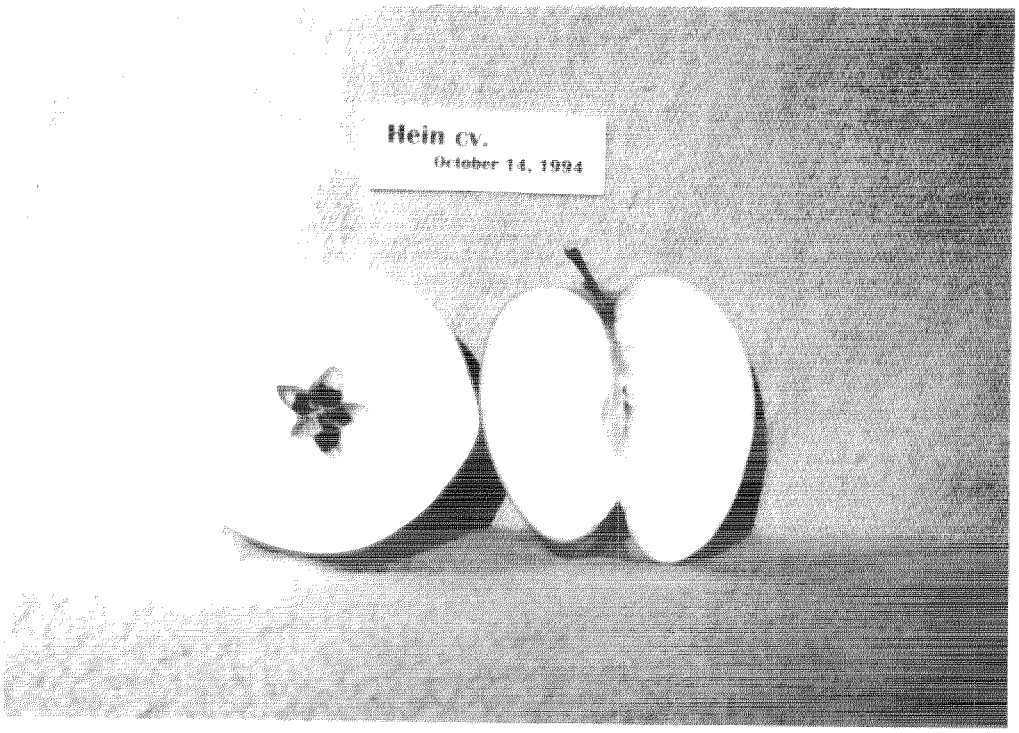
FIG. 1 is a table comparing the Hein cultivar with other Golden Delicious-type varieties.
Figure 8:
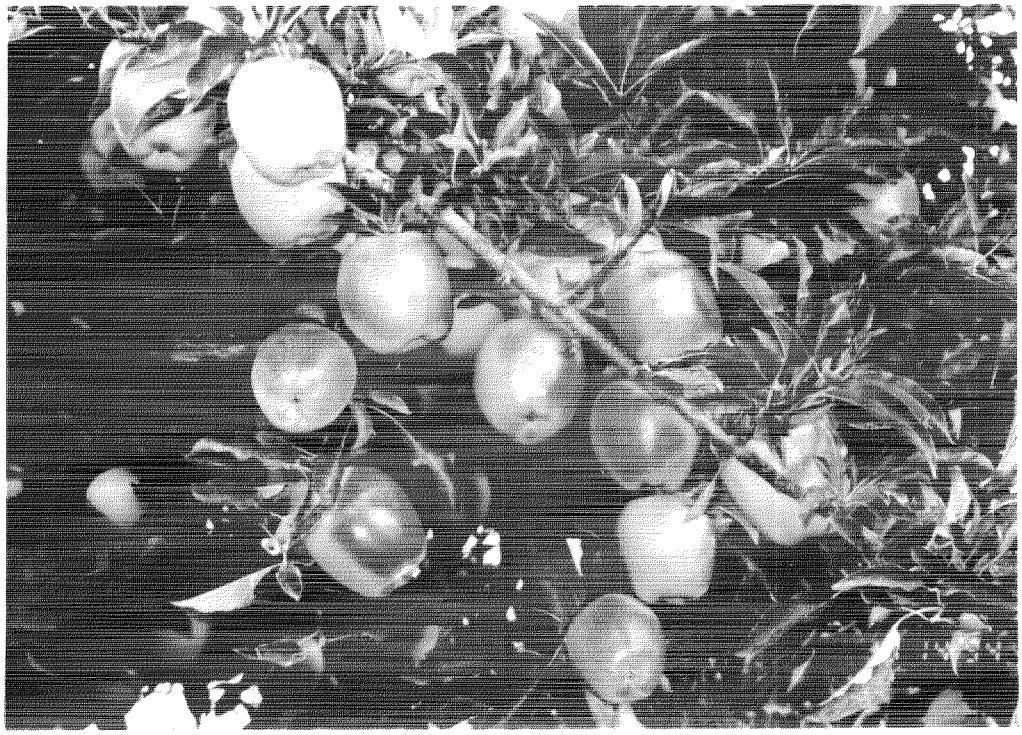
FIG. 8 is a branch of a Hein cultivar just prior to harvest, Oct. 14, 1994.

*Form.*—Round-conical to conical, ribbed, occasionally irregular; five lobes at calyx end, more prominent than those of Golden Delicious, Lucky Rose Golden, or Golden Supreme, but less prominent that those of Red Delicious; more gently rounded than Criterion (see FIG. 6).

*Cavity.*—Depth 15 mm; breadth 25 mm; smooth, acute to acuminate.

*Basin.*—Depth 13 mm; breadth 39 mm; smooth, symmetrical; acute to accuminate, furrowed, lightly pubescent.

*Calyx.*—Open to nearly closed. Segments: Persistent, broadly lanceolate; acute; length 3 mm; separated; erect, lightly reflexed at apex. Outer surface: Pubescent. Inner surface: Pubescent. Eye: Open to partially closed.

*Stem.*—Length average 20 mm; width (breadth) averages 3 mm; shorter and thicker than Golden Delicious (which averages 28 mm in length, 2.2 mm in width); lightly pubescent.

*Skin.*—Medium thickness, smooth, glossy, slightly waxy, free from russet. Dots: Inconspicuous, small, even, circular, evenly distributed over entire surface; white to light cream. Ground color: #25-2 to 25-3, Munsell Color Cascade. Overcolor: Brightly blushed with pink (Munsell #39-7 to 39-11) on exposed fruits. Bloom: Scant. Scarfskin: Absent. General color effect: Attractive bright pink to red blush over creamy green ground color.

*Flesh.*—White with yellowish green tint, juicy, no evidence of water core. Texture Firm, fine-grained, crisp.

*Flavor.*—Mildly subacid to sweet, 12 to 15% soluble solids at proper harvest maturity, mildly aromatic, good to very good.

*Core.*—Longitudinal section ovate to funnel shaped; cross section round, medium size, seed cells closed.

*Seed.*—Normally 8 to 10 total, 2 per cell, dark brown (#32-15 Munsell); length 7 mm; width 4 mm.

*Use.*—Fresh, dessert.

*Storage.*—Superior to Golden Delicious (less tendency to shrivel); 200 days in CA storage; 120 days common storage (32° F.).

Productivity: Moderately productive and annual bearing.

I claim:

1. A new and distinct variety of apple tree substantially as shown and described herein.

* * * * *

FIGURE 1

Comparison of Hein Cultivar with other Golden Delicious-type varieties.

| Variety | Approx. Harvest Date[1] | Tendency To Russet[2] | Stem Length[3] | Shape[4] | Lenticels[5] | Ground Color[6] | Blush[7] |
|---|---|---|---|---|---|---|---|
| Golden Delicious | 0 | 4 | 4 | 3 | 5 | 3 | 2 |
| **Hein Cultivar** | **+14** | **1** | **2** | **4** | **1** | **4** | **4** |
| Golden Supreme | -10 | 3 | 4 | 3 | 4 | 3 | 3 |
| Criterion | +21 | 3 | 4 | 5 | 1 | 3 | 4 |
| Blushing Golden | +12 | 2 | 3 | 3 | 1 | 3 | 5 |
| Lucky Rose Golden | -5 | 1 | 1 | 3 | 2 | 1 | 4 |
| Firmgold | +10 | 2 | 5 | 4 | 2 | 4 | 3 |
| Primegold | 0 | 2 | 3 | 2 | 2 | 3 | 1 |

---

[1] Days + or - Golden Delicious harvest date (9/25/95)

[2] Tendency to russett: 1 = no russett → 5 = severe russet.

[3] Stem length: 1 = <10 mm; 2 = 11-18 mm; 3 = 19-26 mm; 4 = 27-34 mm; 5 = >35 mm.

[4] Shape: 1 = round → 5 = very elongated and conic.

[5] Lenticels: 1 = inconspicuous → 5 = russeted.

[6] Ground color: 1 = white-cream → 3 = cream-yellow → 5 = greenish.

[7] Blush rating: 1 = none → 3 = occasional exposed fruit → 5 = frequently blushed.

UNITED STATES PATENT AND TRADEMARK OFFICE

CERTIFICATE OF CORRECTION

PATENT NO. : Plant 9,907

DATED : June 3, 1997

INVENTOR(S) : R.J. Hein

It is certified that error appears in the above-indentified patent and that said Letters Patent is hereby corrected as shown below:

| COLUMN | LINE | |
|---|---|---|
| 2 | 28 | "minimum" should read --maximum-- |

Signed and Sealed this

Twenty-third Day of September, 1997

*Attest:*

Bruce Lehman

BRUCE LEHMAN

*Attesting Officer*

*Commissioner of Patents and Trademarks*